US009149571B2

(12) United States Patent
Neftel

(10) Patent No.: US 9,149,571 B2
(45) Date of Patent: Oct. 6, 2015

(54) PERITONEAL DIALYSIS SYSTEM

(75) Inventor: Frédéric Neftel, Lausanne (CH)

(73) Assignee: DEBIOTECH S.A., Lausanne (CH)

(*) Notice: Subject to any disclaimer, the term of this patent is extended or adjusted under 35 U.S.C. 154(b) by 231 days.

(21) Appl. No.: 13/507,087

(22) Filed: Jun. 4, 2012

(65) Prior Publication Data
US 2012/0310056 A1 Dec. 6, 2012

Related U.S. Application Data

(62) Division of application No. 10/501,394, filed as application No. PCT/CH03/00048 on Jan. 23, 2003, now abandoned.

(51) Int. Cl.
*A61M 1/28* (2006.01)
*A61M 1/14* (2006.01)

(52) U.S. Cl.
CPC . *A61M 1/28* (2013.01); *A61M 1/14* (2013.01); *A61M 1/287* (2013.01)

(58) Field of Classification Search
CPC .......... A61M 1/14; A61M 1/28; A61M 1/287
USPC ........................................ 604/6.15, 317–318
See application file for complete search history.

(56) References Cited

U.S. PATENT DOCUMENTS

| 2,797,149 | A | * | 6/1957 | Skeggs | 436/53 |
| 3,863,664 | A | * | 2/1975 | Holbrook et al. | 137/205 |
| 4,244,787 | A | * | 1/1981 | Klein et al. | 205/778 |
| 5,199,604 | A | * | 4/1993 | Palmer et al. | 222/25 |
| 5,393,673 | A | * | 2/1995 | Gjerde et al. | 436/171 |
| 5,442,969 | A | * | 8/1995 | Troutner et al. | 73/863.71 |
| 5,788,846 | A | * | 8/1998 | Sternby | 210/647 |
| 5,865,766 | A | * | 2/1999 | Bonsall et al. | 600/578 |
| 6,228,047 | B1 | * | 5/2001 | Dadson | 604/29 |
| 6,595,948 | B2 | * | 7/2003 | Suzuki et al. | 604/29 |

* cited by examiner

Primary Examiner — Quynh-Nhu H Vu
(74) Attorney, Agent, or Firm — Nixon & Vanderhye, PC

(57) ABSTRACT

The invention relates to a peritoneal dialysis sampling system to be used together with a peritoneal dialysis system which is programmed to deliver fluid to a peritoneal cavity of a patient and to drain the fluid from the cavity, said peritoneal dialysis system comprising a supplying line and supplying means for supplying dialysis fluid to the peritoneal cavity, a draining line and draining means for draining the fluid from the cavity, said peritoneal dialysis sampling system comprising an automatic sampling system which is able to automatically sample volumic fractions of the dialysate contained in the peritoneum of the patient at specific time intervals in order to evaluate the peritoneal membrane characteristics and/or improve the peritoneal dialysis for a given patient.

21 Claims, 2 Drawing Sheets

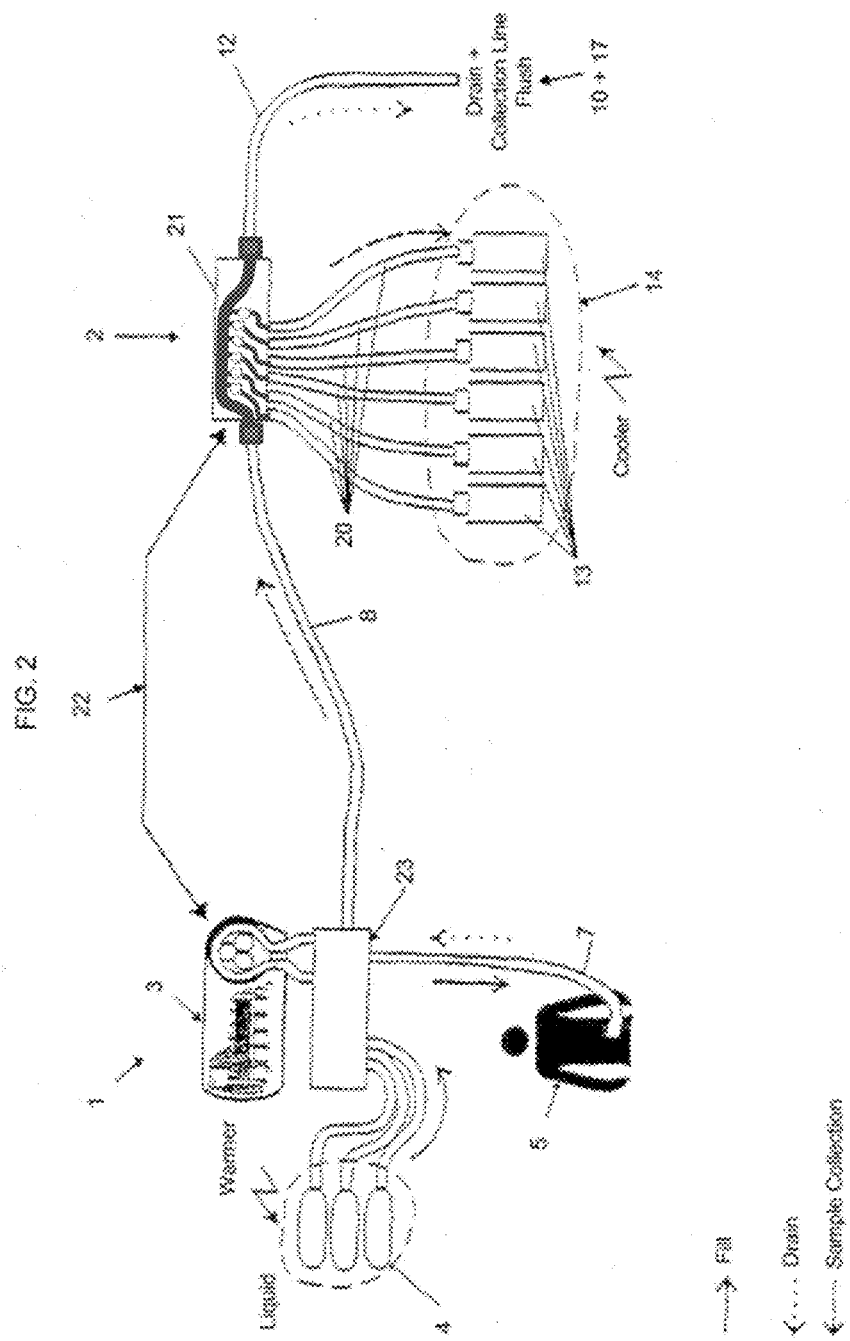

PERITONEAL DIALYSIS SYSTEM

This application is a divisional application from U.S. application Ser. No. 10/501,394, filed on Jul. 15, 2004, now abandoned which is the US national phase of international application PCT/CH03/00048, filed 23 Jan., 2003, which designated the U.S. and claims benefit of PCT/CH02/00046, dated 28 Jan. 2002, the entire contents of each of which are hereby incorporated by reference.

The present invention relates to a peritoneal dialysis sampling system to be used in a peritoneal dialysis system which is programmed to deliver fluid to a peritoneal cavity of a patient and to drain the fluid from the cavity, said peritoneal dialysis system comprising a supplying line and supplying means for supplying dialysis fluid to the peritoneal cavity, a draining line and draining means for draining the fluid from the cavity.

Different tests have been proposed to evaluate the patient membrane characteristics in order to improve the exchanges of fluid during peritoneal dialysis according to each patient. For instance the PDC test according to Haraldsson and Rippe, based on the three pore model, is commonly used to achieve this objective. Other tests would also be of interest if they would be able to evaluate the specific outcome of a given peritoneal dialysis type of cycles for a given patient and be used to improve those cycles based on the peritoneal dialysis outcome.

However all present tests show some inconvenients and limitations. In particular they cannot be reliable enough due to the impossibility of carrying out measurements during certain periods such as dwell time. Those tests are also not able to directly evaluate the outcome of a given type of cycle but rather evaluate the membrane characteristics in order to calculate optimized cycles for the patient. With the PDC test for example, there must be a full exchange cycle before carrying the measurements on the drained volume. State of the art tests also not allow the automatic use of different liquids and/or different concentrations, nor the automatic sampling.

Furthermore they are particularly cumbersome for the patient since they have to be manually done over a 24 h period of time, with typically 5 exchanges. Therefore, the use of those tests is today limited to certain patients and require specific conditions to be conducted.

One of the object of the present invention is to avoid the previous listed problems.

It relates to a peritoneal dialysis sampling system to be used in a peritoneal dialysis system which is programmed to deliver fluid to a peritoneal cavity of a patient and to drain the fluid from the cavity, said peritoneal dialysis system comprising a supplying line and supplying means for supplying dialysis fluid to the peritoneal cavity, a draining line and draining means for draining the fluid from the cavity, said peritoneal dialysis sampling system being characterized by the fact that it consists of an automatic sampling system which is able to automatically sample volumic fractions of the dialysate contained in the peritoneum of the patient at specific time intervals in order to evaluate the peritoneal membrane characteristics and/or improve the peritoneal dialysis for a given patient.

The automatic sampling system is connected on the draining line either between the patient peritoneum and the draining means or between the draining means and a waste collector.

Connecting the automatic sampling system according to the invention on the draining line allows to carry out a test at any time by drawing liquid directly from the peritoneum. It also allows to take samples of fluid at different points of time and having different sample volumes during the same cycle. All these possibilities improve considerably the evaluation of the peritoneal membrane characteristics and/or the peritoneal dialysis outcome for a given patient.

In particular, the possibility to increase the number of sampling steps and automatically vary the dialysate volume and concentration over a certain period of time allows to increase the number of information collected over a limited period of time. As a result, a full and more detailed patient peritoneal membrane evaluation can be made over a shorter period of time, allowing such evaluation to be conducted automatically preferably overnight. In certain circumstances, it may be useful to add one or several more manual samplings over the day, although the more detailed information would have been collected over the night by use of the automatic sampling system according to the present invention.

Preferably the automatic peritoneal dialysis sampling system is provided with means for defining the specific time intervals for sampling volumic fractions in relation with the peritoneal dialysis program sequences.

The evaluation of the peritoneal membrane characteristics may be improved by providing the automatic peritoneal dialysis sampling system with means, e.g. a system of valves and separate fluidic paths, in order to sample different peritoneal dialysis fractions and collect them in separate containers for a later detailed analysis of their specific content.

The automatic peritoneal dialysis sampling system may be connected between the patient peritoneum and the draining means, requiring sampling means to sample liquid from the peritoneum at different points of time. The sampling means may, for example, be of a peristaltic type allowing a precise volumic sampling. Alternatively, the sampling means may result from vacuum originating from the sampling containers which may be controlled by a series of valves, or by gravity. In another embodiment of the present invention the automatic peritoneal dialysis sampling system may be connected after the draining means, such draining means being used, in such case, for both draining the dialysis fluid after each cycle as well as collecting the sampling fractions. In the event of dwell time sampling, the draining means would be activated to sample the volumic fraction required during dwell time, while in the drain phase of each cycle only a fraction of the drainage volume would be collected by use, for example, of a valve system.

The connection of the automatic peritoneal dialysis sampling system to the draining line may also be made by an electromechanical valve which is actuated in relation with a specific functioning of the draining means.

When the connection of the automatic peritoneal dialysis sampling system to the draining line is situated between the patient peritoneum and the draining means, the automatic sampling can be made during the dwell time of the peritoneal dialysis cycle and/or during the drain cycle without interfering with the peritoneal dialysis system. When the connection of the automatic peritoneal dialysis sampling system is situated after the draining means, the automatic sampling can only occur during the drain phase of each cycle or, alternatively, can also occur during the dwell time provided the draining means are activated during such dwell time for that purpose. In the first case, the automatic peritoneal sampling system requires sampling means, while in the latest case the draining means of the peritoneal dialysis system are also used for sampling purposes.

The sampling means, if required, preferably include pumping means such as a peristaltic pump. They may also be of a gravity type, or vacuum type, if in connection with a series of valves.

In a preferred embodiment the automatic sampling system comprises a series of sampling containers, pumping means and a series of valves in order to direct a certain quantity of each fluid sample to a given sampling container.

The sampling containers may consist of soft pouches.

The automatic sampling system may be composed of a series of valves which are controlled by an electronic system in order to direct a certain quantity of each fluid sample to a specific sampling container. The valves may be of electromagnetic type.

Preferably the automatic sampling system comprises means for eliminating a volume of liquid between two samplings at least equivalent to the dead volume contained between the patient and the sampling level. This can be done by providing the system with a purging line. With such a configuration, after a first sampling, the draining line is connected to the purging line in order to purge the above cited dead volume in order to prevent mixing of two different samples. A second sampling occurs then when the draining line is connected to another sampling container. Purging can be obtained either by use of the sampling means or, in the configuration with draining means from the automatic peritoneal dialysis system, by use of such draining means.

Advantageously, both systems: the peritoneal dialysis system which comprises an automatic peritoneal dialysis exchange system, and the automatic peritoneal dialysis sampling system are connected to the patient peritoneum and comprise means for exchanging information together in order for the-automatic peritoneal dialysis sampling system to determine the appropriate timing for each sampling on the basis of the dialysis exchange cycles of the automatic peritoneal dialysis exchange system.

In a further embodiment, the automatic sampling system under the present invention can also be used to not only determine the membrane characteristics but also evaluate one or several peritoneal dialysis exchange cycles in order to determine the best appropriate exchange cycle or series of cycles for the patient.

In a preferred embodiment both automatic peritoneal dialysis sampling system and automatic peritoneal dialysis exchange system are similar systems which are synchronized and which are working with different software and fluidic connections. For instance, they both may comprise peristaltic pumps.

In another preferred embodiment of the present invention, the automatic peritoneal dialysis sampling system only consist of a series of electro-valves and containers, which electro-valves are controlled by the automatic peritoneal dialysis system. In such preferred embodiment, the sampling is directed from the peritoneum to the containers by use of the drawing means of the automatic peritoneal dialysis system which contains a specific order of sequence for the opening and closing of specific valves in connection with the peritoneal dialysis cycles.

The peritoneal dialysis system may comprise a memory key which contains all the necessary data to program the functioning of said automatic peritoneal dialysis sampling system according to the peritoneal dialysis cycles and to store the sampling information.

The automatic peritoneal dialysis sampling system may comprise means for sequentially collecting sample volumes in a tubing, each sample being separated from the previous one by an air bubble inserted by the automatic peritoneal sampling system in-between each sample.

In order to store the samples in optimal conditions until analysis the sampling containers may preferably be enclosed inside a cooling box which comprises cooling means.

Advantageously the automatic peritoneal dialysis sampling system comprises analyzing means for directly analyzing of at least one characteristic of the sample in-line, such as by spectroscopy, fluorometry or by use of chemical or electro chemical means.

The automatic sampling system may be adapted to measure different constituents/parameters such as glucose, urea, creatinine, sodium, chloride, albumine, proteins, osmolarity or ph.

For instance the result of the in-line analysis is used to optimize the next peritoneal dialysis exchange cycle or sampling intervals in order to improve the membrane characteristics evaluation or directly evaluate the impact of specific changes on the peritoneal dialysis outcome for the patient.

Some embodiments of the invention will be discussed hereafter in a more detailed way.

FIG. 2 illustrates another embodiment of the system according to the invention where the automatic sampling system is connected on the draining line between the draining means and a waste collector.

Figure 1:
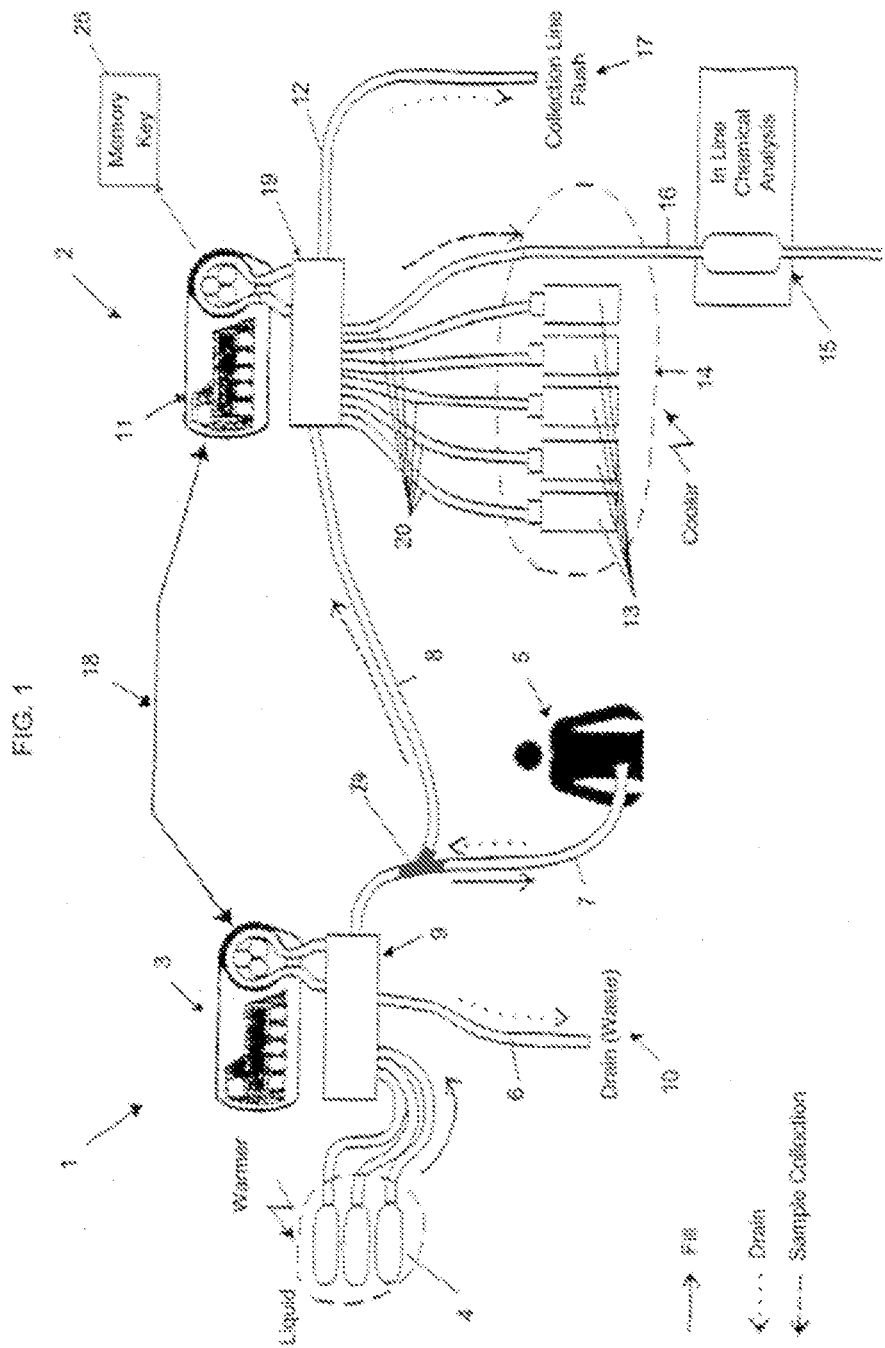
FIG. 1 illustrates a first embodiment of the system according to the invention where the automatic sampling system is connected on the draining line between the patient peritoneum and the draining means.

The peritoneal dialysis system according to FIG. 1 consists of a first system 1 comprising a first peristaltic pump 3, dialysis fluid containers 4, a line 6,7 consisting of a supplying/draining line 7 which is arranged between a patient 5 and the first peristaltic pump 3 and a draining line 6 which is arranged between the first peristaltic pump 3 and a first waste collector 10, the dialysis fluid containers 4 and the draining line 6 may be alternatively connected to the supplying/draining line 7 by a valve 9 e.g. of electromechanical type.

The supplying/draining line 7 is provided with a Y-site 24 in order to connect a sampling line 8.

The peritoneal dialysis system according to FIG. 1 also include an automatic sampling system 2 made of a second peristaltic pump 11, a collection line 12, sampling containers 13 linked to the sampling line 8 via conduits 20 and a analyzing line 16 comprising an analyzing unit 15. The sampling line 8, the conduits 20, the analyzing line 16 and the collection line 12 are all alternatively connected to the second peristaltic pump 11 by an appropriate valve 19.

The sampling containers 13 are arranged within a cooling container 14.

Both first system 1 and the automatic sampling system 2 may change information via a communication line 18 (by cable or by wireless communication). The automatic sampling system 2 is provided with a memory key 25 which contains all the necessary data to program the functioning of said automatic peritoneal dialysis sampling system and to store the sampling information.

The automatic sampling system 2 can be programmed to take volumic fractions of liquid at predetermined times, for instance during the dwell time. Those volumic fractions may differ from each others.

The volumic fractions may also be taken during the drain cycle.

The collection line 12 allows to purge a dead volume between samplings.

FIG. 2 shows another configuration, very similar to the configuration of FIG. 1, but which uses only one peristaltic pump 3 for supplying dialysis liquid to the patient, draining dialysis fluid from the patient and supplying volumic fractions to the automatic sampling system 2. In this configuration, the sampling line 8 is connected on the draining line 6. In said configuration, sampling are controlled by the peristaltic pump which may be activated for sampling purposes at any time, including during the dwell time.

Of course the invention is not limited to the above detailed embodiments. Generally it covers any automatic sampling system 2 which can take volumic fractions of liquid during a dwell cycle or a drain cycle.

The invention claimed is:

1. An automatic peritoneal dialysis sampling process comprising:
    performing a peritoneal dialysis treatment comprising a dwell phase and a drain phase
    automatically sampling, at specific time intervals, volumic fluid fractions of a dialysate contained in a peritoneum of a patient to evaluate a peritoneal membrane characteristic of the peritoneum and/or improve a peritoneal dialysis for the patient,
    employing a peritoneal dialysis sampling system comprising a series of sampling containers, pump, and a series of valves that direct a certain quantity of each fluid fraction sample of dialysate taken from the peritoneum of the patient to a specific sampling container in the series of sampling containers; wherein the employed system comprises a supplying line and a supply container for supplying dialysis to a peritoneal cavity, a draining line and a drain container for draining the fluid from said peritoneal cavity, and a connecting port for allowing a connection to a Y-site on the draining line which is situated between the patient peritoneum and the drain container; and
    allowing the automatic sampling to occur during the dwell time of the peritoneal dialysis cycle and/or during the drain cycle in order to improve the evaluation of the peritoneal membrane characteristics and/or improve the peritoneal dialysis for the patient.

2. The process according to claim 1 comprising allowing use of different peritoneal dialysis liquids and/or different concentrations for each exchange cycle.

3. The process according to claim 1 comprising allowing the automatic sampling during a dwell time of a peritoneal dialysis cycle and/or during a drain cycle.

4. The process according to claim 1, wherein the valves are an electromagnetic type.

5. The process according to claim 1, wherein said pump is a peristaltic type.

6. The process according to claim 1, wherein the employed system comprises a connecting port for connecting the system to the draining line before the drain container in order to collect samples of specific drain cycles.

7. The process according to claim 1 comprising eliminating a volume of liquid between two samplings at least equivalent to a dead volume of the fluid contained in the fluidic pathway between the patient and a sampling level.

8. The process according to claim 1, wherein the employed system comprises an automatic peritoneal dialysis exchange system, wherein both automatic peritoneal dialysis sampling system and automatic peritoneal dialysis exchange system are connected to the patient peritoneum and comprises a communication line for exchanging information together in order for the automatic peritoneal dialysis sampling system to determine the appropriate timing for each sampling on the basis of the dialysis exchange cycles of the automatic peritoneal dialysis exchange system.

9. The process according to claim 8, wherein both automatic peritoneal dialysis sampling system and automatic peritoneal dialysis exchange system are synchronized between each other.

10. The process according to claim 1, wherein the employed system comprises a memory key which contains all necessary data to program a functioning of said automatic peritoneal dialysis sampling system and to store the sampling information.

11. The process according to claim 1, wherein the sampling containers consist of soft pouches.

12. The process according to claim 1, wherein the sampling containers contain a vacuum in order to draw the liquid automatically when in open connection with the drawing line.

13. The process according to claim 1, wherein said sampling containers are enclosed inside a cooling box which comprises a cooling device to maintain the samples in optimal condition for storage until analysis.

14. The process according to claim 1, comprising directly analyzing at least one characteristic of the sample in-line, such as by spectroscopy, fluorometry, or by use of chemical or electro-chemical analysis.

15. The process according to claim 14, wherein said directly analyzing allows the measurement of at least one of the following constituents or characteristics: glucose, urea, creatinine, Sodium, Chloride, albumine, proteins, osmolarity, or ph.

16. The process according to claim 14 comprising using the result of the in-line analysis to optimize the next peritoneal dialysis exchange cycle or sampling intervals in order to improve the membrane characteristics evaluation and/or improve the peritoneal dialysis for the patient.

17. The process according to claim 16 comprising defining the specific time intervals for sampling volumic fractions in relation with the peritoneal dialysis program sequences.

18. The process according to claim 1 comprising using different peritoneal dialysis liquids and/or different concentrations for each exchange cycle, whether it is a tidal exchange or a full exchange cycle.

19. The process according to claim 1 comprising eliminating a volume of liquid at least equivalent to the dead volume contained between the patient and the sampling level between two samplings.

20. An automatic peritoneal dialysis sampling process comprising:
    automatically sampling, at specific time intervals, volumic fluid fractions of a dialysate contained in a peritoneum of a patient to evaluate a peritoneal membrane characteristic of the peritoneum and/or improve a peritoneal dialysis for the patient,
    employing a peritoneal dialysis sampling system comprising a series of sampling containers, a pump, and a series of valves that direct a certain quantity of each fluid fraction sample of dialysate taken from the peritoneum of the patient to a specific sampling container in the series of sampling containers; and
    preventing a mixing of two different samples by eliminating a volume of liquid of the fluid contained in the fluidic pathway between the patient and the sampling level between two samplings.

21. An automatic peritoneal dialysis sampling process comprising:
    performing a peritoneal dialysis treatment comprising a dwell phase and a drain phase,
    automatically sampling, at specific time intervals, volumic fluid fractions of a dialysate contained in a peritoneum of a patient to evaluate a peritoneal membrane characteristic of the peritoneum and/or improve a peritoneal dialysis for the patient,
    employing a peritoneal dialysis sampling system comprising a series of sampling containers, a pump, and a series of valves that direct a certain quantity of each fluid fraction sample of dialysate taken from the peritoneum of the patient to a specific sampling container in the series of sampling containers; and performing the automatic samplings during the dwell time of the peritoneal dialysis cycle and/or during the drain cycle.

* * * * *